United States Patent

Peterson et al.

Patent Number: 5,879,314
Date of Patent: Mar. 9, 1999

[54] TRANSDUCER ASSEMBLY AND METHOD FOR COUPLING ULTRASONIC ENERGY TO A BODY FOR THROMBOLYSIS OF VASCULAR THROMBI

[75] Inventors: Thomas M. Peterson; Pal Dharmendra, both of Erie, Pa.; Eugene DeCastro, Jamestown, N.Y.

[73] Assignee: Cybersonics, Inc., Erie, Pa.

[21] Appl. No.: 922,188

[22] Filed: Sep. 2, 1997

Related U.S. Application Data

[63] Continuation of Ser. No. 885,338, Jun. 30, 1997, abandoned.

[51] Int. Cl.⁶ .................................................. A61B 17/22
[52] U.S. Cl. .................................................. 601/2
[58] Field of Search ........................ 601/2–4; 600/439; 604/22

[56] References Cited

U.S. PATENT DOCUMENTS

| | | | |
|---|---|---|---|
| 4,986,275 | 1/1991 | Ishida et al. | 601/3 |
| 5,072,722 | 12/1991 | Granz | 600/439 |
| 5,195,509 | 3/1993 | Rentschler et al. | 601/4 |
| 5,222,483 | 6/1993 | Plisek | 601/4 |
| 5,624,382 | 4/1997 | Oppelt et al. | 601/2 |

*Primary Examiner*—Ruth S. Smith
*Attorney, Agent, or Firm*—Walter A. Hackler

[57] ABSTRACT

A transducer assembly and method for coupling ultrasonic energy to a body for thrombolysis of vascular thrombi is provided. The assembly includes a catalytic transducer for transmitting ultrasound into a medical target transcutaneously. The catalytic transducer includes a front mass having structure which optimizes the transmission of ultrasound into the body. A reservoir for containing a cooling conductive medium between the front mass and the body surface is provided, and is contained within the housing. In addition, the catalytic transducer includes an irrigation manifold, disposed through a center of the front mass, for directing the media into the reservoir generally along a perimeter thereof. The front mass includes an apex for accumulating expelled gasses. A sloped surface of the front mass functions to direct expelled gasses toward the apex and through an outlet provided by the irrigation manifold. The medium may be circulated from a degassing tank as well as a heat exchange unit in order to maintain a desired reservoir temperature at the body surface.

12 Claims, 3 Drawing Sheets

TRANSDUCER ASSEMBLY AND METHOD FOR COUPLING ULTRASONIC ENERGY TO A BODY FOR THROMBOLYSIS OF VASCULAR THROMBI

This is a continuation of U.S. patent application Ser. No. 08/885,338, filed on Jun. 30, 1997, now abandoned.

The present invention relates to noninvasive medical treatment of vascular thrombi using ultrasound in conjunction with therapeutic agents.

Reperfusion of an occluded coronary artery in a patient having acute myocardial infarction has been conventionally achieved by either intravenous administration of thrombolytic therapy agents, such as streptokinase, or by percutaneous transcatheter mechanical devices, such as balloon angioplasty devices.

While administration of thrombolytic agents is currently the most widely used reperfusion therapy, the use of thrombolytic agents presents several unresolved problems. Such agents provide inadequate treatment in many cases. For example, it has been found that typically, the initial reperfusion rate is only about 70%, and TIMI grade III flow is achieved in less than 60% of patients. Furthermore, intermittent reperfusion and reocclusion of the infarct related artery is frequent, and substantial time is necessary to achieve successful recanalization. In addition, about 30% of patients presenting with acute myocardial infarction are excluded from thrombolytic agent therapy due to the risk of bleeding complications. In spite of this, thrombolytic agent therapy is still associated with significant hemorrhage complications in five to six percent of patients.

On the other hand, while the success rate of reperfusion with primary angioplasty techniques is high, due to the prolonged time that it usually takes to start the procedure, the time from arrival at the hospital to reperfusion may be prolonged. Therefore, there is a need for the development of safe, non-invasive techniques which can achieve effective and rapid reperfusion, and can be initiated immediately upon arrival at the hospital, or even before admission.

Destruction of thrombosis and other medical targets, including cancerous growths and calcifications, in a living being may be obtained through the use of ultrasound by induced hyperthermia, or thermal heating of the target tissues, or by the effects of cavitation, or both. Hyperthermia is due to acoustic absorption of the tissue which converts mechanical energy of the acoustic wave into thermal energy. Living cells, including cells of cancerous tumors, are destroyed by the heating effect of ultrasound. In addition, high energy ultrasound applied to fluids generates vapor filled microbubbles, or "cavities", with the concomitant expansion and collapse of the cavities, accompanied by local intense hydraulic shock which leads to fragmentation or dissolution of a medical target, such as a thrombosis, i.e. blood clot.

A more recent development in the medical use of ultrasound for treatment of medical targets in a living being involves the use of ultrasound in conjunction with therapeutic, i.e. medicinal, agents. It has been found that low frequency ultrasound has the effect of accelerating activity of thrombolytic agents injected near the site of an occlusion in an artery. Thus, it is believed that ultrasound has a synergistic effect on such medicinal agents and consequently, a lower dosage of medicinal agent coupled with ultrasound therapy can be used as a substitute for conventional therapies which rely primarily on the use of drugs alone. Consequently, it is possible to minimize the administrative amount of medicinal agent, and thus reduce undesirable side effects that may be attributable to the agent.

In order to generate the high temperatures, or the level of cavitation, needed for cell destruction or plaque fragmentation, high energy ultrasound is required, which can lead to destruction of healthy tissue if not properly managed.

U.S. Pat. No. 5,269,291 issued on Dec. 14, 1993 to Carter which is incorporated herein by this specific reference thereto, describes a miniature ultrasonic transducer for plaque ablation. The miniature traducer is sized for intravascular positioning such that the transducer may be inserted in a vessel and is positioned directly adjacent a clot or plaque. Thus, high energy ultrasonic waves may be generated from within the vessel and radiated directly into the medical target.

A number of transcutaneous and endocavity ultrasound probes have been designed for transmitting ultrasound through a body surface of a patient in order to treat a medical target beneath the body surface. Studies have shown that transcutaneous ultrasound in conjunction with low dose medicinal agents, for example, streptokinase, enhances thrombolysis in animals in vivo, however skin and soft tissue damage induced by ultrasound energy passing through skin and soft tissues has been a major limitation.

U.S. Pat. No, 5,485,839 issued on Jan. 23, 1996 to Aida et al. incorporated herein by this specific reference thereto, discloses a method and apparatus for ultrasonic wave medical treatment using computed tomography. This invention includes an ultrasonic wave applicator which transmits therapeutic ultrasonic waves transcutaneously. In one embodiment, the ultrasonic applicator may be an endocavity probe which includes a water bag being placed in contact with the patient during the treatment. Aida et al teaches that water in the water bag may function as a coolant for preventing potential damage to an intestinal wall of a patient by excessive heating.

Another patent which discloses an therapeutic ultrasonic device which includes a water bag for placement on a body surface is U.S. Pat. Ser. No. 5,307,816 issued on May 3, 1994 to Hashimoto et al., which is also incorporated herein by this specific reference thereto. Hashimoto discloses a thrombus resolving treatment apparatus which may be useful for treating a thrombus, or blood clot with noninvasive, external radiation of therapeutic ultrasound in conjunction with administration of a thrombus resolving agent. A water bag or jelly pad positioned between the ultrasonic radiator and a body surface of a patient.

U.S. Pat. No. 5,601,526, issued on Feb. 11, 1997 to Chapelon et al. and incorporated herein by this specific reference thereto, discloses an ultrasonic transducer including a membrane filled with refrigerated fluid, such as degassed water, where the membrane is placed in contact with the skin in order to protect the skin from excessive heat. Chapelon discloses that the cooling water may be circulated to maintain an intended cooling temperature.

It is, therefor, generally known to those skilled in the art that deaerated water is a satisfactory coupling medium which can be circulated in order to provide protection to healthy tissues. Unfortunately, however, it has been found that circulation of the water as well as the vibration of the ultrasonic probe causes increased expulsion of gasses from the water. Gasses expelled from the water, or other coupling fluid, while the fluid is in the ultrasonic field may significantly impair conductivity, and cause attenuation of the ultrasonic wave.

The present invention provides an improved ultrasonic transducer assembly and method which addresses this problem, and other problems encountered with the use of conventional devices which will later become apparent. As will be discussed in detail hereinafter, the apparatus and method of the present invention is designed to remove expelled gasses in a cooling medium while the medium is within the ultrasonic transducer probe and circulated through the ultrasonic field.

SUMMARY OF THE INVENTION

Accordingly, a ultrasonic medical transducer apparatus and method for coupling ultrasonic energy to a body for medical therapy is provided by the present invention. The apparatus may comprise an assembly of components, including an ultrasonic transducer, hereinafter sometimes referred to as a "catalytic transducer", as it may be used as a catalyst for accelerating the activity of medicinal agents.

The catalytic transducer includes a housing, and means, such as a piezoelectric element, for generating ultrasonic waves in response to, for example, a electrical signal supplied by an external power source. In addition, the transducer comprises a front mass disposed in the housing and a radiator for directing the ultrasonic waves into a medical target in a patient.

Importantly, a reservoir is provided in the housing for containing a fluid conductive medium, i.e. a coupling medium, between the front mass and the a body surface of a patient. The medium provides means for coupling the ultrasonic waves with the body surface. The reservoir may comprise a flexible membrane or bladder.

The fluid conductive medium is circulated into the transducer reservoir from an external tank which contains a replenishing supply of the medium and may include means for degassing the medium, for example by vacuum sonification.

Importantly, the assembly is designed to manage a flow of the conductive medium into and out of the reservoir in a manner which provides optimal transmission of ultrasonic energy. More specifically, means are provided for accumulating and removing expelled gasses from the reservoir. The flow management means is defined by a front mass surface area which is preferably an arcuate, concave surface area. The concave surface area includes an apex for enabling gasses expelled as the medium flows into the reservoir, to accumulate at the apex. An outlet in fluid communication with the reservoir means and disposed generally at the apex, provides means for passing fluid conductive medium and accumulated gasses out of the reservoir, which may be circulated back to the tank.

The flow management means additionally includes inlet means for directing fluid conductive medium into the reservoir. Preferably, coupling fluid being circulated into the transducer will pass between the front mass and the transducer housing and into the reservoir generally along a perimeter of the concave surface area.

Further, the flow management means may include an irrigation manifold in fluid communication with the reservoir and having means for directing flow of circulating fluid conductive medium into and out of the reservoir. The irrigation manifold manages the flow of fluid in such a way as to reduce the amount of expelled gasses present in the ultrasonic field and additionally provide sufficient dwell time of conductive fluid in the field. Preferably, the irrigation manifold includes an outlet disposed at the concavity apex such that gasses accumulated at the concavity apex will pass into an outlet conduit provided by the irrigation manifold and rise toward the back end of the transducer, i.e. upward from the reservoir. The irrigation manifold may have an inlet for directing the fluid conductive medium into the reservoir at the perimeter of the concave surface area.

In addition, the catalytic transducer may be precisely positioned on a body surface of a patient by means of a flexible, articulating arm connected to a back end of the transducer housing. Advantageously, the flexible arm may contain cannulas or the like for providing fluid communication between the supply tank and the transducer. In addition, electrical wiring for providing electrical connection between the transducer and the external power source may be contained within the flexible arm. This design keeps an operator's work area free of irrigation cannulas and electrical wiring.

Means for cooling the fluid conductive medium is preferably provided, which includes means for circulating the medium between the reservoir and a cooling source, such as a refrigerated tank.

Advantageously, the catalytic transducer housing may include means for focusing the focal point of the ultrasonic wave. More particularly, the housing may include a subhousing, such as a shroud, adjustably engaged to a base portion of the housing. The shroud may be threadably engaged to the base portion such that, after the transducer is placed on the body surface, the focal depth of the radiated ultrasonic energy may be finely adjusted by rotation of the shroud with respect to the base portion.

In order to maintain a fixed position of the focal point, the reservoir membrane and fluid conductive medium is containable within the shroud when the transducer is placed against a body surface. Thus, the shroud functions to contain the fluid-filled membrane and prevent the membrane from distending outside the transducer housing.

Preferably, the shroud is engaged to the base portion forward of the piezoelectric element which is preferably contained within the base portion of the housing. The structure of the present invention is designed to reduce resonance vibrations of the transducer, thus enabling more accurate focusing and preventing destruction of the device from overheating.

The design of the present invention, described briefly hereinabove, provides a transducer assembly having structure which optimizes transmission of high energy ultrasonic waves through a coupling medium by providing for efficient removal of expelled gasses while the medium is in the ultrasonic field.

BRIEF DESCRIPTION OF THE DRAWINGS

The present invention will be more clearly understood with reference to the following detailed description when considered in conjunction with the accompanying drawings of which.

DETAILED DESCRIPTION

Figure 1:
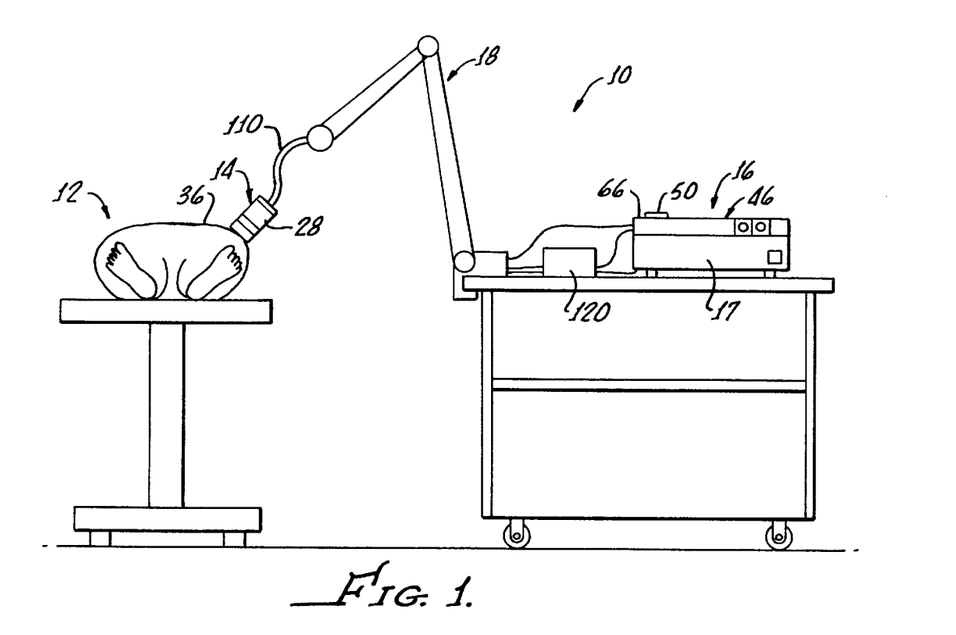
FIG. 1 shows an ultrasonic medical transducer assembly, including a catalytic transducer, suitable for performing a method for coupling ultrasonic energy to a body for destruction of blood clots, or other medical targets, in accordance with the present invention.

Turning now to FIG. 1, an ultrasonic medical transducer assembly 10 is shown which is suitable for performing a method for coupling ultrasonic energy to a body 12 for medical therapy in accordance with the present invention. The assembly 10 generally comprises a catalytic transducer 14 and may also comprise a generator unit 16, including a generator 17 for driving the catalytic transducer 14. The generator unit 16 powering the transducer 14 may be operable by standard 110v AC 50/60 hz, but may be modified to accommodate any line voltage, as the AC is converted to DC by the generator. An articulating arm 18 may be provided as means for positioning the transducer 14 on the body 12.

Figure 2:
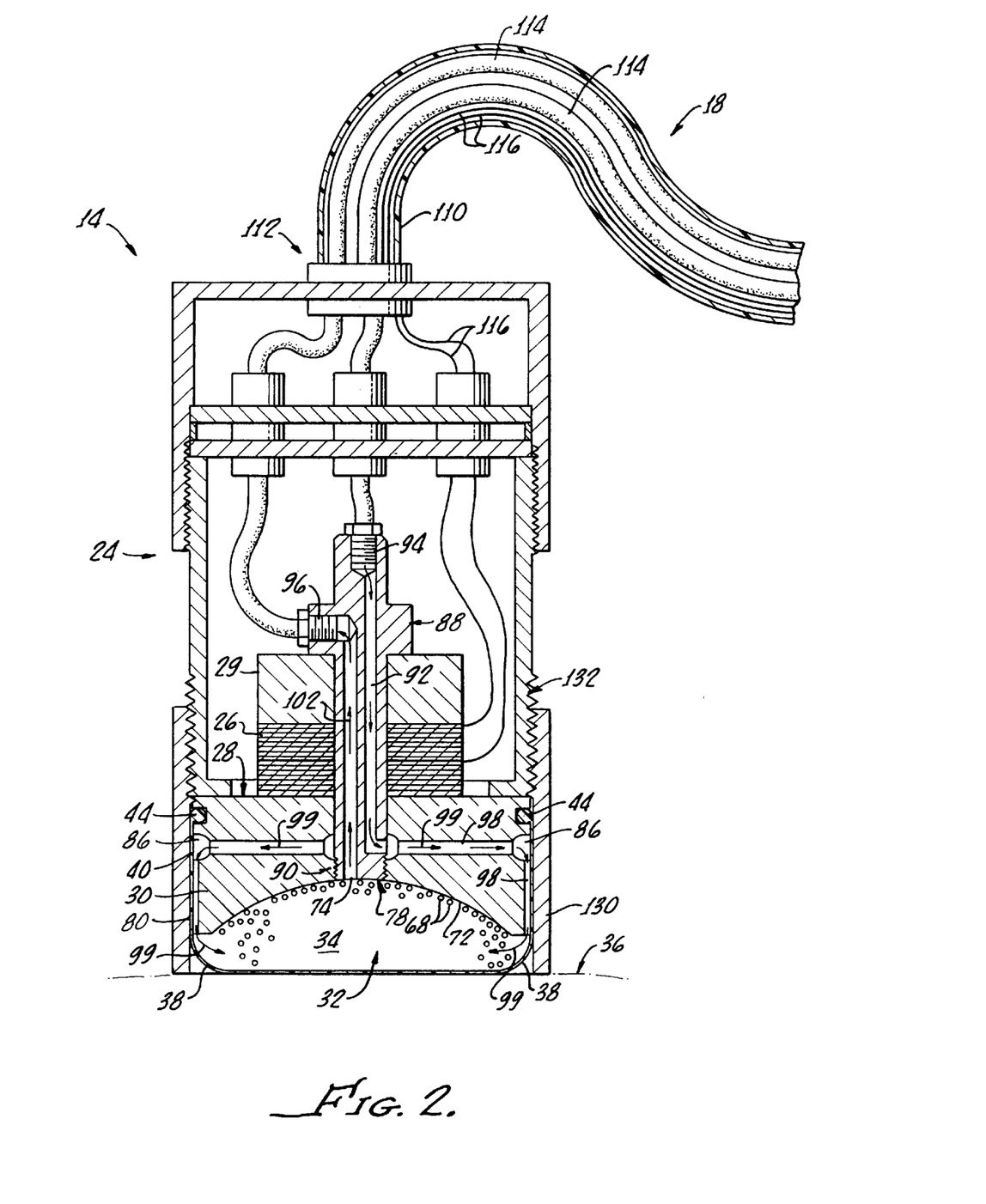
FIG. 2 shows a cross-sectional view of the catalytic transducer shown in FIG. 1, said catalytic transducer including means for accumulating and removing gasses from a fluid conductive medium in the ultrasonic field.

The catalytic transducer 14 is shown in greater detail in FIG. 2. Importantly, the transducer 14 may be used as a catalyst for, and as an adjunct to, injected chemical agents for dissolving arterial thrombi. The dosage of a chemical agent may be introduced at a level below its threshold of performance and then the agent is acted upon by the ultrasonic energy in the thrombus area to increase the effectiveness of the agent and shorten the time required to dissolve the thrombus.

The transducer 14 generally comprises a housing 24, and a piezoelectric element 26 or other suitable means for generating ultrasonic waves. The transducer 14 includes a front mass 28 and a back mass 29 which may be comprised of, for example, aluminum, stainless steel or titanium or another suitable material. The front mass 28 provides means 30 for radiating the ultrasonic energy generated by the piezoelectric elements 26 into the body 12.

The ultrasonic energy is preferably applied within the frequency range of about 20 kHz to about 130 kHz. The generator 17 preferably produces a frequency range of about 18 kHz to about 100 kHz and provides a pulse for a given frequency of about 30 Hz to about 480 Hz and a frequency sweep of plus or minus 4 kHz. Wattage output from the generator is variable from 5 to 200 watts. Wattage output from the transducer 14 may be from about one watt per square centimeter to about 30 watts per square centimeter.

The front mass 28 includes structure which optimizes the transmission of ultrasonic energy, as will be discussed hereinafter. The front mass 28 may have a diameter from between about 1.75 inches to about six inches.

A reservoir 32 is provided for containing a fluid conductive medium 34 between the front mass 28 and a body surface 36 of the patient 12 and for coupling ultrasonic energy therewith. The transducer 14 is designed to be placed directly on the body surface 36 such that the reservoir 32 provides an interface between the front mass 28 and the body surface 36. The reservoir 32 may be comprised of a flexible membrane 38 in the form of a pocket or bladder connected at an open end 40 thereof to the front mass 28 by a fluid tight seal 44.

The medium 34 may comprise water or another suitable fluid conductive medium. Turning back now to FIG. 1, the assembly 10 may include a tank 46 which holds a replenishing supply of the fluid conductive medium 34. The tank 46 may include a port 50 for providing access to the tank 46 for filling thereof.

Figure 3:
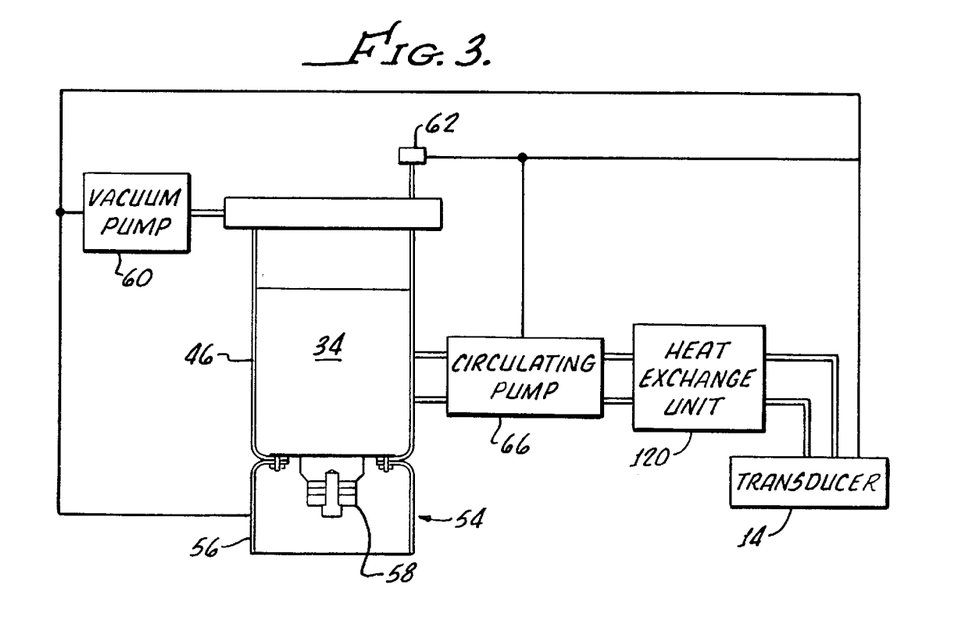
FIG. 3 shows a diagrammatical view of the medical transducer assembly including cooling means for maintaining a comfortable temperature at a body surface of the patient.

The tank 46 preferably includes means for degassing the fluid conductive medium 34 within the tank 46. FIG. 3 shows the tank 46 and means for degassing which may comprise for example, a ultrasonic vacuum reservoir portion 56 of the tank 46 including a degassing transducer 58 which functions to remove gasses from the medium 34 by vacuum sonification as will be readily understood by those in the art. Further included is a vacuum pump 60 for supplying vacuum required for the degassing, as well as a vent valve 62 for releasing expelled gasses into the atmosphere. A circulating pump 66 may be provided for circulating the fluid conductive medium 34 from the tank 46 to the catalytic transducer 14 and for maintaining fluid pressure in the reservoir 32.

Importantly, as will now be discussed in detail, the present invention is designed such that a flow of the circulating medium 34 may be managed in such a way as to provide optimal transmission of ultrasonic energy thorough the medium 34 in the reservoir 32. Turning back to FIG. 2, the catalytic transducer 14 includes means for accumulating and removing expelled gasses 68 from the transducer reservoir 32. Thus, in addition to the means for degassing the medium 34 in the external supply tank 46, gasses are also removed from the medium while in the transducer 14, and more particularly, while in the ultrasonic field.

The flow management means is defined by a surface area 72 of the front mass 28 which is preferably arcuate in cross-section and includes concavity means, comprising a concavity apex 78, for accumulating the gasses expelled from the fluid conductive medium 34. The arcuate surface area enables gasses 68 within the reservoir 32 to coarse freely upward toward the apex as they are expelled from the medium 34.

Importantly, the surface area 72 includes outlet means 74 for removing fluid conductive medium from the reservoir and the gasses expelled therefrom. As shown in FIG. 2, the reservoir outlet 74 is disposed generally at the apex 78 of the surface area 72. Thus, the outlet 74 enables gasses accumulated at the apex to pass through the surface area 72 and out of the reservoir 32.

The flow management means also includes inlet means 86 for directing fluid conductive medium into the reservoir 32, generally along a perimeter 80 of the arcuate surface area 72.

Upon entering the reservoir through the relatively narrow inlet means 86, gasses are expelled from the medium 34 and are initially concentrated along a reservoir boundary 82. Consequently, a significant portion of the reservoir 32 is kept relatively clear of gas bubbles 68, which enhances transmission of ultrasound therethrough. Due to the sloping surface 72 of the front mass 28, the gas bubbles are rapidly propelled upward and through the outlet 74.

Advantageously, the flexible membrane 38 will maintain a wide breadth as a result of the inward flow of medium 34 along the membrane 38, i.e. the reservoir boundary 82, providing optimal contact thereof with the body surface 36.

Preferably, the transducer 14 includes an irrigation manifold 88 for directing flow of the medium 34. The irrigation manifold 88 may be disposed generally through a center 90 of the front mass 28 as shown. More particularly, the irrigation manifold 88 includes an inlet conduit 94, in fluid communication with the inlet means 86, for directing the medium 34 supplied by the tank into the reservoir 32 and an outlet conduit 96, in fluid communication with the outlet 74, for removing the medium and gasses from the reservoir. In this embodiment, the front mass 28 may include one or more bores 98 therethrough for directing the inward flow of medium 34 into the reservoir boundary 82 as shown. Thus, the medium 34 will flow into the reservoir 32 in a flow path represented by arrows 99, and the medium 34 as well as expelled gasses 68 will pass from the reservoir 32 in flow path represented by arrows 102 in FIG. 2.

It should be appreciated that although the fluid medium 34 is degassed prior to being circulated to the transducer 14 as discussed hereinabove, the circulation of the medium 34 through constrictions within the transducer 14 as well as vibrations of the transducer 14 tends to promote further expulsion of gasses. The present invention manages the flow of the medium 34 in a way which reduces the impact of the expelled gasses within the reservoir 32 by allowing the gasses 68 to accumulate at the apex 78 and be rapidly removed therefrom.

FIG. 1 shows the arm 18 of the transducer assembly 10. The arm 18 may be articulated, or jointed and preferably includes a flexible portion 110 connected to a back end 112 of the transducer 14 which provides means for precise positioning of the transducer 14 on the body surface 36 of the patient 12. As shown in FIG. 2, the flexible portion 110 of the arm 18 may be designed to contain cannulas or conduits 114 which provide for the circulation of the fluid medium 34 into and out of the transducer 14. Insulated electrical wiring 1 16 for providing electrical communication between the generator unit 16 and the transducer 14 may also be disposed through the flexible arm 110. By containment of the conduits 114 and wiring 116 in the arm 110, an operator's work area is kept clear and unobstructed.

Means for circulating the medium between the reservoir and a cooling source may be provided in order to maintain a cool temperature at the body surface in contact with the transducer 14. For example, the replenishing tank 46 may be refrigerated in a conventional manner. Alternatively, as shown in both FIGS. 1 and 3, a heat exchange unit 120 may be provided for cooling the medium 34 as it is circulated out of the tank 46 after the medium has been degassed by vacuum sonification.

Preferably, if the fluid conductive medium is water, the medium is cooled to a temperature of between about 32° F. and about 40° F. to enable a range of between about 60° F. and about 70° F. to be maintained at the irrigation manifold and front mass. This temperature range is comfortable to the patient and also prevents overheating of the transducer 14.

As the fluid medium 34 flows through the irrigation manifold 88 and reservoir 32 heat will be absorbed by the manifold 88 and front mass 30. As shown in FIG. 2, the irrigation manifold and front mass have structure which optimizes heat absorption during inward flow of the cooling medium 34 and provides sufficient dwell time of the medium within the ultrasonic field.

More particularly, the flow path 99 defined by inlet conduit 94 and bores 98 which passes cooled fluid medium 34 into the reservoir 32, functions to provide a surface area of contact for optimal heat transfer to occur. Thus, heat generated in the transducer 14 will be rapidly conducted into the flowing cooled medium 34, warming the medium and cooling the transducer 14. Thus, as discussed hereinabove, although the medium 34 is initially cooled to between about 32° F. and about 40° F., the heat absorbed by the transducer elements cause the medium 34 in the reservoir 32 to be maintained at a comfortable range of between about 60° F. and about 70° F. The outlet conduit 96 promotes rapid removal of the warmed conductive media 34 by providing a relatively brief flow path out of the reservoir 32, and eventually back to the tank 46 for degassing and cooling.

In order to diminish resonance vibrations of the transducer 14, a shroud 130 is adjustably engaged to a base portion 132 forward of the piezoelectric element 26 as shown in FIG. 2.

Figure 4:
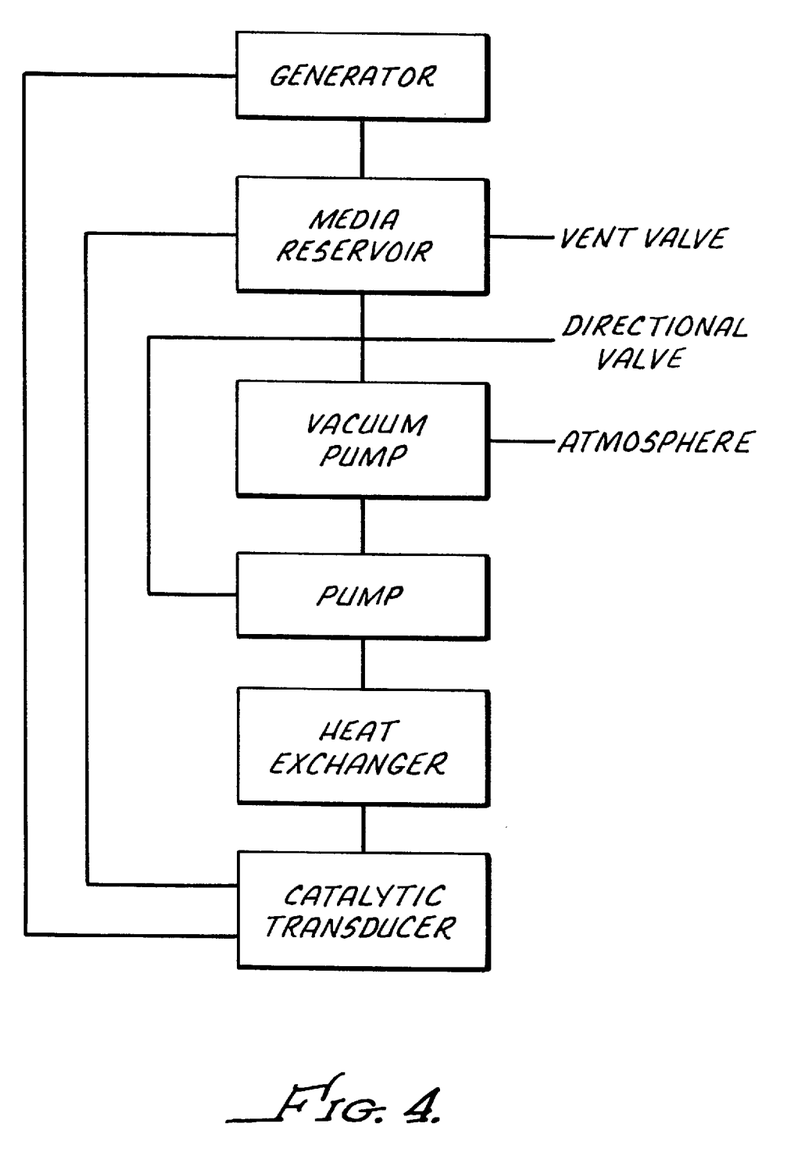
FIG. 4 shows a block diagram of a transducer assembly in accordance with the present invention.

FIG. 4 shows a block diagram of an embodiment of the present invention in order to illustrate potential connections between components of the transducer assembly.

It should be appreciated that although a transcutaneous ultrasonic transducer has been hereinabove described, with appropriate modification thereof, the present invention may encompass an endocavity probe incorporating the novel features hereinabove described.

A method for coupling ultrasonic energy to a body for dissolution or treatment of a medical target, such as vascular thrombi or the like, in accordance with the present invention generally comprises the steps of positioning the ultrasonic transducer 14 described hereinabove onto a body surface 12 over a medical target, radiating ultrasound waves from the ultrasonic transducer 14 into a medical target beneath the body surface in order to treat the medical target, and accumulating and removing gasses 68 expelled from the circulating fluid conductive medium as described in detail hereinabove. Preferably, the method further comprising the step of disposing a medicinal agent adjacent the medical target prior to the step of radiating ultrasound waves.

EXAMPLE

Animal preparation. The American Physiological Society Guidelines for Animal Research were followed, which conform to the position of the American Heart Association on Research Animal Use adopted by the Association in November of 1984. Fifteen adult New Zealand White rabbits weighing 3.5 to 4.5 kg were anesthetized and maintained with Ketamine (20 mg/kg) and Xylazine (3.0 mg/kg) administered intravenously. The right carotid artery was cannulated with a 5 F arterial sheath and a 3.5 F coronary Tracker catheter (Target, San Jose, Calif.). A coronary guide wire was inserted through the carotid arterial sheath to the iliofemoral artery. Selective angiography was performed at a baseline to demonstrate both iliofemoral arteries.

Thrombus preparation-induction of thrombolytic occlusion. Briefly, a 0.014 inch coronary guide wire was advanced into the proximal part of the iliofemoral artery with 1 centimeter beyond a tip of the Tracker catheter. A positive electrode of a 3 volt battery was connected to the guidewire and a negative electrode to the rabbits skin. Electrical interference on a electrocardiographic monitor indicated that an electric shock was established. Occlusion was induced in both iliofemoral arteries in random order. Thrombotic occlusion of the artery was confirmed by selective angiography.

Experimental protocol. After angiographic documentation of bilateral total occlusion of the iliofemoral arteries, Streptokinase (25,000 units/kg) was administered intravenously. Then, one iliofemoral artery with either the older of the younger thrombus was randomized to transcutaneous ultrasound whereas the contra lateral artery served as a control. After 15 minutes of ultrasound treatment, angiography was repeated for documentation of potency in both sides. If the ultrasound treated artery was still occluded, an additional 15 minute ultrasound therapy was repeated, up to a total of four periods of fifteen minutes. When reperfusion occurred, heparin (1,000 U) was administered intravenously, and the rabbit was followed for an additional 60 minutes with repeated angiography every 15 minutes to document potency of both the iliofemoral arteries.

Controls. Two control groups were studied to assess the potential of ultrasound mediated damage to skin, soft tissue and artery as detected by gross inspection, histology, and biochemical measurements. Group 1 consisted of five rabbits in which transcutaneous ultrasound was applied to the left carotoid artery after 30 minutes prior to the iliofemoral thrombus induction. In a second control group consisting of four rabbits, there was no attempt at thrombus induction, however, ultrasound was applied for one hour above the area of the left or right iliofemoral arteries. Plasma levels of creatine kinase (CK), lactate dehydrogenase (LDH) and a total red blood cell counts (RBC) were checked at baseline, after 3 minutes and after 60 minutes of ultrasound application, and 60 minutes thereafter.

A transducer assembly in accordance with the present invention was used that operates at approximately 37 kHz, and utilizes both pulse and sweep frequencies, 91 kHz and ±2 kHz, respectively. The power can range to 160 watts and to prevent tissue damage from both such high outputs a transducer designed in accordance with the present invention was utilized, including the irrigation manifold and the reservoir to provide for efficient cooling and coupling to the skin. The overall dimension of the transducer apparatus is about 7.0 cm in length and about 4.0 cm in diameter which can be easily positioned over the selected site.

Skin Temperature. Temperature was measured with a subcutaneous needle thermistor in the ultrasound treated area and was recorded every one minute during ultrasound therapy.

Pathological studies. After the experiments, all rabbits were euthanized by induction of intravenous KCL. The iliofemoral arteries, ultrasound exposed skin and soft tissues, as well as the left carotoid artery and overlying skin and soft tissues were excised, examined grossly and then fixed in 10% neutral buffered formalin for 24–72 hours. The iliofemoral and left carotoid arteries were the cut transversely every 2 mm for the length of the vessel. Samples were dehydrated in graded alcohol, cleared in Hemo-De®, and embedded in the paraffin. Sections four to five $\mu$m thick were cut and mounted on glass slides and stained with hematoxylin-eosin. The preparations were examined macroscopically and microscopically for presence of thermal injury, and for the potency of iliofemoral arteries. The preparations were examined in random order, with the examiner blinded to whether the artery was treated or not with ultrasound.

Statistical analysis. Data are given as mean values ±SD. Repeated measurements were performed to assess serum CK, LDH levels and RBC counts at three different time courses. A p value $\leq 0.05$ was considered statistically significant.

Results. Six out of fifteen (40%) ultrasound treated arteries were recanalized after one fifteen minute treatment period, four more arteries (26.7%) reperfused after additional 15 minutes of ultrasound therapy, and all fifteen arteries were patent after four fifteen minute ultrasound therapy periods. In contrast, only one of the contra lateral arteries, i.e. those arteries that were not treated with ultrasound but were treated with streptokinase alone, were recanalized during the same period.

After initial recanalization of the treated arteries, heparin was administered intravenously and the arterial patency was assessed by repeated angiography every fifteen minutes for a total of one hour. One of the ultrasound treated arteries (6.7%) reoccluded fifteen minutes after initial recanalization, whereas one of the control arteries recanalized fifteen minutes after heparin administration and another one at 30 minutes after heparin administration. None of the ultrasound treated or control arteries has distal embolization or occlusion of distal branches on repeated angiography. The skin temperature ranged from 25° to 33° C. during the application of transcutaneous ultrasound.

Biochemical and hemological findings. As shown in Table 1A, there was no increase in serum LDH and no decrease in the RBC after ultrasound treatment compared to the baseline. The serum CK was increased to 18% (p=NS) compared to the baseline after electrical induction of thrombus and then rose slightly to 12% (p=NS) after ultrasound treatment.

TABLE 1A

Comparison of serum CK, LDH levels and RBC[1]

|  | CK (IU/L) | LDH (IU/L) | RBC ($10^6$/L) |
| --- | --- | --- | --- |
| Baseline | 916 ± 399 | 245 ± 228 | 5.4 ± 0.7 |
| After electrical induction | 1123 ± 499 | 234 ± 209 | 6.3 ± 0.4 |
| After ultrasound treatment | 1283 ± 449 | 234 ± 171 | 5.9 ± 0.9 |
| P value | p = NS | p = NS | p = NS |

[1]CK — creatine kinase;
LDH — lactate dehydrogenase;
RBC — total red blood cell count As shown in Table 1B, the data from the control group 2 suggest that ultrasound treatment alone did not result in muscle damage or hemolysis.

TABLE 1B

Comparison of serum CK, LDH levels and RBC counts in control group 2

|  | CK (IU/L) | LDH (IU/L) | RBC ($10^6$/L) |
| --- | --- | --- | --- |
| Baseline | 688 ± 166 | 136 ± 60 | 5.9 ± 0.7 |
| After 30 minutes ultrasound treatment | 534 ± 60 | 91 ± 31 | 5.7 ± 0.6 |
| After 60 minutes ultrasound treatment | 568 ± 70 | 103 ± 14 | 6.0 ± 0.8 |
| 60 minutes thereafter | 613 ± 96 | 114 ± 37 | 5.8 ± 0.8 |

Histopathology. Histopathology revealed that arteries that were patent by angioplasty were also patent by microscopy with only focal residual mural thrombosis, whereas arteries which remained occluded until the end of protocol showed occlusive thrombi. Small microscopic areas of focal necrosis were found in the arterial walls in all vessels. The magnitude of vessel injury was the same in the ultrasound treated arteries as in the control arteries. There was no evidence of damage or inflammation in the skin or soft tissues overlying the ultrasound treated iliofemoral arteries. In addition, in control group 1, there was no evidence of thermal injury or inflammation in the arteries and overlying skin and soft tissues, after continuous exposure for thirty minutes to ultrasound treatment four to five hours before sacrifice; nor was there evidence of tissue damage in any of the four rabbits in control group 2 which had sixty minutes of ultrasound exposure to a non-thrombosed iliofemoral artery.

Discussion. This study shows that with the newly designed ultrasound transducer in accordance with the present invention, transcutaneous ultrasound can significantly augment lysis of arterial thrombi without associated tissue damage. Recanalization was achieved by low dose streptokinase alone in only 1 (6.7%), and an additional two arteries after administration of heparin. In contrast, all fifteen arteries (100%) were reperfused within fifteen of ultrasound administration. The rate of reocclusion within sixty minutes after initial recanalization by ultrasound was low (6.7%). As an ultrasonic wave propagates through a medium it is progressively absorbed and energy is converted to heat. Mechanical and cavitation effects cause an elevation in temperature. The increase in temperature is strongly related to the mode, frequency efficiency and intensity in which ultrasound is applied. In general, ultrasound energy delivered with a continuous mode, lower frequency, and higher power intensity results in higher temperature.

While transcutaneous ultrasound has a synergistic effect on thrombus disruption when combined with streptokinase or a media containing microbubbles is known, use of the present invention prevents significant thermal damage to skin and soft tissues and no necrosis of the vessel wall was found histologically after ultrasound application with the present invention.

The examples discussed hereinabove utilized an ultrasonic transducer apparatus including a reservoir containing a coupling cooling media, in accordance with the present invention, which omitted a concentrated beam of high powered ultrasound in a pulsed mode Importantly, as hereinabove stated, there was no histological evidence of ultrasound mediated damage to overlying skin, soft tissues or arteries.

Serum CK activity is a particularly rapid and sensitive marker for muscle damage and LDH is present in large concentration in erythrocytes as well as tissues. Muscle damage and hemolysis may result in an increase in the serum CK and LDH levels respectively, as well as a decrease in RBC counts. The data given in the Tables above show that there is no increase in LDH levels and no decrease in RBC counts after ultrasound treatment compared to the baseline, which indicates that there is no hemolysis after electrical induction and ultrasound treatment. The CK level was increased to 18% compared to baseline after electrical induction of thrombus and then rose slightly after ultrasound treatment, focally microscopic necrosis was found in the vessel wall by histology. This indicates that electricity and/or ultrasound might induce vascular muscle damage. However, in the control group 2, there was no increase in CK levels compared to he baseline after 30 minutes and 60 minutes of ultrasound treatment alone and in addition, there was no evidence of vessel damage in this control group. This suggests that in this rabbit thrombosis model, the electrical induction of thrombus and concomitant tissue coagulation, rather than ultrasound, results in mild muscle damage.

Although there has been hereinabove described a transducer assembly and method for coupling ultrasonic energy to a body, in accordance with the present invention, for the purpose of illustrating the manner in which the invention may be used to advantage, it will be appreciated that the invention is not limited thereto. Accordingly, any and all modifications, variations, or equivalent arrangements which may occur to those skilled in the art should be considered to be within the scope of the invention as defmed in the appended claims.

What is claimed is:

1. Ultrasonic medical apparatus comprising:
    a housing:
        means, including a piezoelectric element, enclosed in said housing for generating ultrasonic waves;
        a front mass disposed in said housing;
        means for radiating the ultrasonic waves into a medical target in a patient;
        reservoir means including a flexible membrane for containing a fluid conductive medium between the front mass and the flexible membrane to thereby provide an interface between said fluid conductive medium and a body surface of a patient and for coupling the radiated ultrasonic waves into the body surface;
    a fluid conductive medium contained in said reservoir means; and
    flow management means, defining an arcuate surface area on said front mass, for accumulating and removing expelled gasses from the reservoir means in order to enhance the transmission of the ultrasonic waves into the medical target, said arcuate surface area comprising concavity means, including an concavity apex, for enabling gasses expelled from the fluid conductive medium to accumulate at the concavity apex, and outlet means, in fluid communication with said reservoir means and disposed generally at said concavity apex, for passing fluid conductive medium and accumulated gasses out of the reservoir means.

2. The ultrasonic medical apparatus according to claim 1 wherein the flow management means further includes inlet means for directing fluid conductive medium into the reservoir means adjacent a perimeter of the front mass surface area.

3. The ultrasonic medical apparatus according to claim 1 wherein the flow management means includes an irrigation manifold disposed through the front mass, said irrigation manifold including both inlet means for directing fluid conductive medium into the reservoir means adjacent a perimeter of the front mass surface area, and outlet means for passing expelled gasses out of the reservoir means through generally the concavity apex.

4. The ultrasonic medical apparatus according to claim 1 further comprising a cooling source and cooling means for maintaining a desired temperature at the body surface of the patient, said cooling means including means for circulating the fluid conductive medium between the reservoir means and the cooling source.

5. The ultrasonic apparatus according to claim 4 further comprising flexible arm means, connected to a back end of the housing, for positioning the ultrasonic medical apparatus on the body surface of the patient, and wherein said means for circulating is disposed through the flexible arm means.

6. Ultrasonic medical apparatus comprising:
    a housing;
    means, including a piezoelectric element, enclosed in said housing for generating ultrasonic waves;
    front mass means, disposed in said housing, for radiating the ultrasonic waves into a medical target in a patient;
    a fluid conductive medium;
    reservoir means including a flexible membrane containing the fluid conductive medium between the front mass means, the flexible membrane providing an interface between said fluid conductive medium and the body surface of the patient,
    flow management means, defined by an outlet through the front mass means, for removing expelled gasses from the reservoir means in order to enhance the transmission of the ultrasonic waves into the medical target, said front mass means including a sloped surface comprising concavity means, including a concavity apex, for enabling gasses expelled from the fluid conductive medium to accumulate at the concavity apex, and outlet means, in fluid communication with said reservoir means and disposed generally at said concavity apex, for passing fluid conductive medium and accumulated gasses out of the reservoir.

7. The ultrasonic medical apparatus according to claim 6 wherein the flow management means further comprises inlet means for directing the fluid conductive medium into the reservoir means along a boundary thereof.

8. The ultrasonic medical apparatus according to claim 6 further comprising a cooling source and cooling means for maintaining a desired temperature at the body surface of the patient, said cooling means including means for circulating the fluid conductive medium between the reservoir means and the cooling source.

9. A method for coupling ultrasonic energy to a body for dissolution or treatment of a medical target the method comprising the steps of:

positioning an ultrasonic transducer having a radiator comprising a front mass having an arcuate or sloped surface onto a body surface over the medical target;

radiating ultrasound waves from the ultrasonic transducer into the medical target beneath the body surface to thereby dissolve or treat the medical target;

containing a fluid conductive medium in the transducer by confining the fluid conductive medium in a reservoir between the arcuate or sloped surface of the radiator and the body surface;

circulating the fluid conductive medium between a replenishing source of fluid conductive medium and the transducer;

accumulating, in the transducer reservoir, gasses expelled from the circulating fluid conductive medium; and removing the accumulating gasses from the transducer reservoir through outlet means disposed generally at the apex of said sloped or arcuate surface of the radiator.

10. The method according to claim 9 further comprising the step of disposing a medicinal agent adjacent the medical target prior to the step of radiating ultrasound waves.

11. The method according to claim 9 further comprising the step of cooling the fluid conductive medium during the step of circulating the fluid conductive medium.

12. The method according to claim 9 wherein the step of circulating comprises the steps directing fluid conductive medium into the transducer reservoir along a perimeter of the reservoir and passing the directed fluid conductive medium and accumulated gasses from the reservoir through generally a center of the reservoir and returning said directed fluid to the replenishing source.

* * * * *